(12) United States Patent
Batooie

(10) Patent No.: US 11,845,735 B2
(45) Date of Patent: Dec. 19, 2023

(54) METHOD FOR SYNTHESIZING (RS)-WARFARIN

(71) Applicant: Nasim Batooie, Kermanshah (IR)

(72) Inventor: Nasim Batooie, Kermanshah (IR)

( * ) Notice: Subject to any disclaimer, the term of this patent is extended or adjusted under 35 U.S.C. 154(b) by 0 days.

(21) Appl. No.: 17/971,959

(22) Filed: Oct. 24, 2022

(65) Prior Publication Data

US 2023/0167079 A1    Jun. 1, 2023

Related U.S. Application Data

(60) Provisional application No. 63/283,479, filed on Nov. 28, 2021.

(51) Int. Cl.
*C07D 311/56*    (2006.01)

(52) U.S. Cl.
CPC .................. *C07D 311/56* (2013.01)

(58) Field of Classification Search
CPC ................................................ C07D 311/56
See application file for complete search history.

(56) References Cited

U.S. PATENT DOCUMENTS

| | | | | |
|---|---|---|---|---|
| 2,427,578 A | * | 9/1947 | Stahmann | C07D 311/46 549/285 |
| 5,686,631 A | * | 11/1997 | Li | C07D 311/56 549/285 |

* cited by examiner

*Primary Examiner* — Golam M Shameem
(74) *Attorney, Agent, or Firm* — Bajwa IP Law Firm; Haris Zaheer Bajwa

(57) ABSTRACT

A method for synthesizing (RS)-Warfarin comprising preparing a liquid mixture, wherein the liquid mixture comprises trihexyltetradecylphosphonium bromide, methyl salicylate, acetyl chloride, benzaldehyde, and acetone. The method may further comprise incubating the liquid mixture at a temperature between 20° C. and 30° C. for a time duration between 26 and 34 minutes, and forming (RS)-Warfarin by adding water to the incubated liquid mixture with a volume ratio (water:incubated liquid mixture) between 1:1 and 1.5:1.

13 Claims, 8 Drawing Sheets

METHOD FOR SYNTHESIZING (RS)-WARFARIN

CROSS-REFERENCE TO RELATED APPLICATION

This application claims the benefit of priority from U.S. Provisional Patent Application Ser. No. 63/283,479, filed on Nov. 28, 2021, entitled "METHOD FOR ONE-POT SYNTHESIS OF WARFARIN IN THE PRESENCE OF PHOSPHORUS IONIC LIQUID AT AMBIENT TEMPERATURE" which is incorporated herein by reference in its entirety.

TECHNICAL FIELD

The present disclosure is generally related to an exemplary method for synthesizing (RS)-Warfarin, and more particularly to an exemplary method for synthesizing (RS)-Warfarin in a one-pot reaction.

BACKGROUND

Warfarin is an anticoagulant commonly prescribed to treat and prevent embolism and thrombosis. Warfarin prevents blood clot formation by repressing a vitamin K-mediated biosynthesis pathway which may lead to the synthesis of blood clotting proteins. Conventionally, Warfarin may be synthesized by Michael addition of benzylideneacetone to 4-hydroxycoumarin in the presence of a base. Notwithstanding, many variations in the reaction of hydroxycoumarin with benzylideneacetone have been reported to improve the procedure and efficiency of Warfarin synthesis.

Conventional methods for producing Warfarin may have different drawbacks, including but not limited to, prolonged reaction duration, low product yields, and reaction dependency to toxic solvents. Thus, there is need to develop a solvent-free method capable of producing high yields of Warfarin in a one-pot reaction which may result in an improved efficiency, decreased reaction time, more environment-friendly reaction procedure, and less reactant consumption.

SUMMARY

This summary is intended to provide an overview of the subject matter of the present disclosure, and is not intended to identify essential elements or key elements of the subject matter, nor is it intended to be used to determine the scope of the claimed implementations. Its sole purpose is to present some concepts of one or more exemplary aspects in a simplified form as a prelude to the more detailed description that is presented later. The proper scope of the present disclosure may be ascertained from the claims set forth below in view of the detailed description below and the drawings.

One or more exemplary embodiments describe an exemplary method for synthesizing an exemplary (RS)-Warfarin. An exemplary method may comprise preparing an exemplary liquid mixture comprising trihexyltetradecylphosphonium bromide, methyl salicylate, acetyl chloride, benzaldehyde, and acetone. In an exemplary embodiment, an exemplary method may further comprise incubating an exemplary liquid mixture at a temperature between 20° C. and 30° C. for a time duration between 26 and 34 minutes, and forming an exemplary (RS)-Warfarin by adding water to an exemplary incubated liquid mixture with a volume ratio (water:incubated liquid mixture) between 1:1 and 1.5:1.

In one or more exemplary embodiments, preparing an exemplary liquid mixture may include preparing an exemplary liquid mixture comprising trihexyltetradecylphosphonium bromide with an exemplary concentration between 50.5% (w/w) and 53% (w/w), methyl salicylate with an exemplary concentration between 17.5% (w/w) and 19.5% (w/w), acetyl chloride with an exemplary concentration between 8.5% (w/w) and 10.5% (w/w), benzaldehyde with an exemplary concentration between 11.5% (w/w) and 14% (w/w), and acetone with an exemplary concentration between 6.5% (w/w) and 7.5% (w/w).

This Summary may introduce a number of concepts in a simplified format; the concepts are further disclosed within the "Detailed Description" section. This Summary is not intended to configure essential/key features of the claimed subject matter, nor is intended to limit the scope of the claimed subject matter.

BRIEF DESCRIPTION OF THE DRAWINGS

The novel features which are believed to be characteristic of the present disclosure, as to its structure, organization, use and method of operation, together with further objectives and advantages thereof, will be better understood from the following drawings in which an exemplary embodiment will now be illustrated by way of example. It is expressly understood, however, that the drawings are for the purpose of illustration and description only and are not intended as a definition of the limits of the present disclosure. Exemplary embodiments will now be described by way of example in association with the accompanying drawings in which.

DETAILED DESCRIPTION

In the following detailed description, numerous specific details are set forth by way of examples to provide a thorough understanding of the relevant teachings related to the exemplary embodiments. However, it should be apparent that the present teachings may be practiced without such details. In other instances, well known methods, procedures, components, and/or circuitry have been described at a relatively high-level, without detail, in order to avoid unnecessarily obscuring aspects of the present teachings.

The following detailed description is presented to enable a person skilled in the art to make and use the methods and devices disclosed in one or more exemplary embodiments of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary implementations will be plain to one skilled in the art, and the general principles defined herein may be applied to other implementations and applications without departing from the scope of the present disclosure. The present disclosure is not intended to be limited to the implementations shown, but is to be accorded the widest possible scope consistent with the principles and features disclosed herein.

Disclosed herein is an exemplary method for synthesizing (RS)-Warfarin, $C_{19}H_{16}O_4$, in an exemplary one-pot reaction. In one or more exemplary embodiments, one-pot reaction may refer to a reaction in which all exemplary reactants may be subject to consecutive chemical reactions in a same reactor. An exemplary one-pot reaction may be much straightforward and may prevent lengthy separation and purification processes of exemplary intermediate compounds. Thus, an exemplary one-pot reaction may improve efficiency of an exemplary chemical reaction, save resources and time, and result in a high chemical yield.

Figure 1:
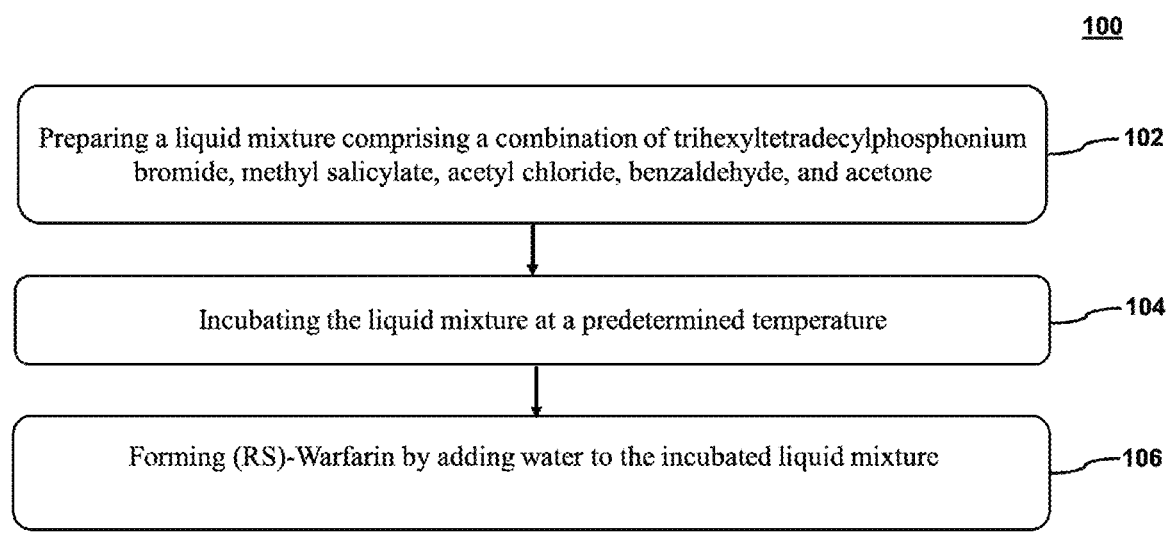
FIG. 1 shows an exemplary flowchart of an exemplary method for synthesizing an exemplary (RS)-Warfarin, consistent with one or more exemplary embodiments of the present disclosure.

FIG. 1 shows an exemplary flowchart of exemplary method 100 for synthesizing an exemplary (RS)-Warfarin, consistent with one or more exemplary embodiments of the present disclosure. In one or more exemplary embodiments, (RS)-Warfarin ($C_{19}H_{16}O_4$) refers to a racemic mixture of two exemplary active enantiomers—i.e., R-form and S-form. Warfarin may refer to 4-hydroxy-3-(3-oxo-1-phenylbutyl)-2H-1-benzopyran-2-one which may be used as an exemplary anticoagulant drug to avoid blood clot formation and blood clot migration. Warfarin may also be known as Coumadin®, Coumafene, Prothromadin, Zoocoumarin, Coumarins, 4-Hydroxy-3-(3-oxo-1-phenylbutyl)coumarin, 3-(1'-Phenyl-2'-acetylethyl)-4-hydroxycoumarin, 1-(4'-Hydroxy-3'-coumarinyl)-1-phenyl-3-butanone, 3-(alpha-Acetonylbenzyl)-4-hydroxycoumarin, 4-hydroxy-3-(3-oxo-1-phenylbutyl)chromen-2-one, etc.

Referring to FIG. 1, exemplary method 100 may comprise: preparing an exemplary liquid mixture comprising an exemplary combination of trihexyltetradecylphosphonium bromide, methyl salicylate, acetyl chloride, benzaldehyde, and acetone (step 102); incubating exemplary liquid mixture at an exemplary predetermined temperature (step 104); and forming exemplary (RS)-Warfarin by adding water to an exemplary incubated liquid mixture (step 106).

Figure 2:
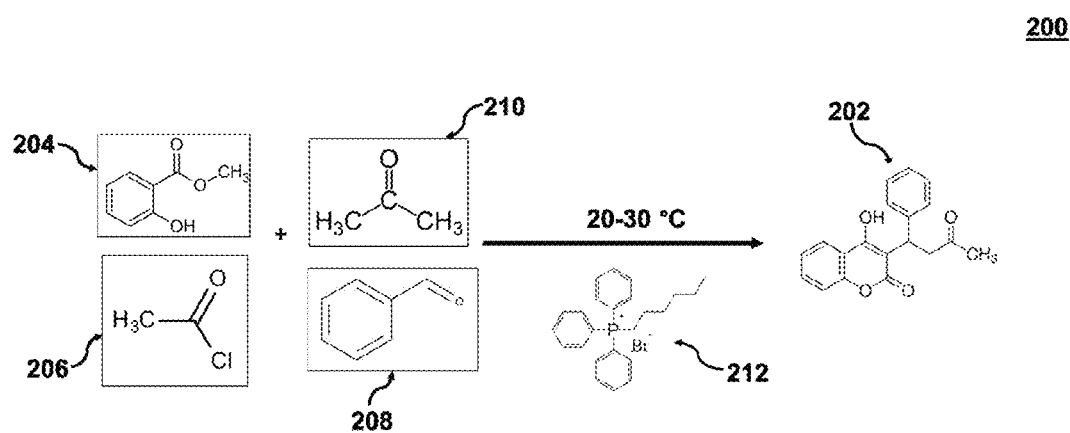
FIG. 2 illustrates an exemplary schematic representation of an exemplary one-pot reaction for forming an exemplary (RS)-Warfarin, consistent with one or more exemplary embodiments of the present disclosure.

In further detail, step 102 may include preparing an exemplary liquid mixture comprising an exemplary combination of trihexyltetradecylphosphonium bromide, methyl salicylate, acetyl chloride, benzaldehyde, and acetone. FIG. 2 illustrates an exemplary schematic representation of exemplary one-pot reaction 200 for forming exemplary (RS)-Warfarin 202, consistent with one or more exemplary embodiments of the present disclosure. In one or more exemplary embodiments, exemplary one-pot reaction 200 may include exemplary precursors including methyl salicylate 204, acetyl chloride 206, benzaldehyde 208, acetone 210, and trihexyltetradecylphosphonium bromide 212 that may be added to an exemplary laboratory container including, but not limited to, beakers, tins, flasks, bottles, buckets, basins, bowls, vials, tubes, barrels, cannisters, etc.

In one or more exemplary embodiments, referring to step 102 of exemplary method 100, preparing an exemplary liquid mixture may include adding methyl salicylate, acetyl chloride, benzaldehyde, acetone, and trihexyltetradecylphosphonium bromide to an exemplary laboratory container, such as a beaker, with an exemplary molar ratio (methyl salicylate:acetyl chloride:benzaldehyde:acetone:trihexyltetradecylphosphonium bromide) of about 1:1:1:1:1, while stirring at about 20-25° C. for a predetermined time duration (e.g., 30 min) using a stirrer, e.g., a magnetic stirrer. In an exemplary embodiment, preparing an exemplary liquid mixture may include adding about 0.1-0.2 g methyl salicylate, about 0.07-0.08 g acetyl chloride, about 0.1-0.15 g benzaldehyde, about 0.05-0.06 g acetone, and about 0.4-0.5 g trihexyltetradecylphosphonium bromide to an exemplary laboratory container, such as a beaker, while stirring at about 20-25° C. for a predetermined time duration (e.g., 30 min) using a stirrer, e.g., a magnetic stirrer.

Figure 3:
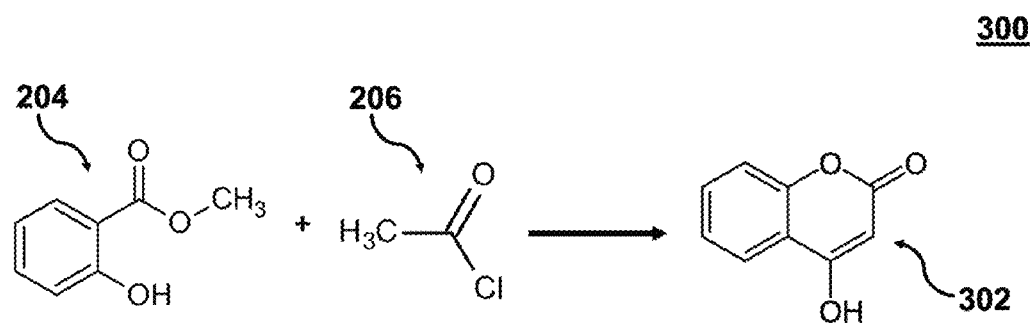
FIG. 3 illustrates an exemplary schematic representation for forming 4-Hydroxycoumarin through an exemplary reaction between methyl salicylate and acetyl chloride, consistent with one or more exemplary embodiments of the present disclosure.

With further regards to step 102 of exemplary method 100, in an exemplary embodiment, an exemplary liquid mixture may comprise methyl salicylate ($C_8H_8O_3$) with an exemplary concentration between about 17.5% (w/w) and 19.5% (w/w). In an exemplary embodiment, an exemplary liquid mixture may comprise methyl salicylate with an exemplary concentration of about 18.5% (w/w). In one or more exemplary embodiments, exemplary liquid mixture may comprise acetyl chloride ($C_2H_3ClO$) with an exemplary concentration between about 8.5% (w/w) and 10.5% (w/w). In an exemplary embodiment, exemplary liquid mixture may comprise acetyl chloride with an exemplary concentration of about 9.6% (w/w). In an exemplary embodiment, an exemplary reaction may be occurred, in an exemplary laboratory container, between methyl salicylate and acetyl chloride resulting in the formation of 4-Hydroxycoumarin, $C_9H_6O_3$. FIG. 3 illustrates exemplary schematic representation 300 for forming 4-Hydroxycoumarin 302 through an exemplary reaction between methyl salicylate 204 and acetyl chloride 206, consistent with one or more exemplary embodiments of the present disclosure.

With further regards to step 102, in one or more exemplary embodiments, exemplary liquid mixture may comprise benzaldehyde, $C_6H_5CHO$, with an exemplary concentration between 11.5% (w/w) and 14% (w/w). In an exemplary embodiment, an exemplary liquid mixture may comprise benzaldehyde with an exemplary concentration of about 12.9% (w/w). In one or more exemplary embodiments, benzaldehyde may be substituted with 4-nitrobenzaldehyde, 4-methoxybenzaldehyde, 4-methylbenzaldehyde, 3-nitrobenzaldehyde, 4-chlorobenzaldehyde, or 4-bromobenzaldehyde. In one or more exemplary embodiments, an exemplary liquid mixture may comprise acetone, $(CH_3)_2CO$, with an exemplary concentration between 6.5% (w/w) and 7.5%

Figure 4:
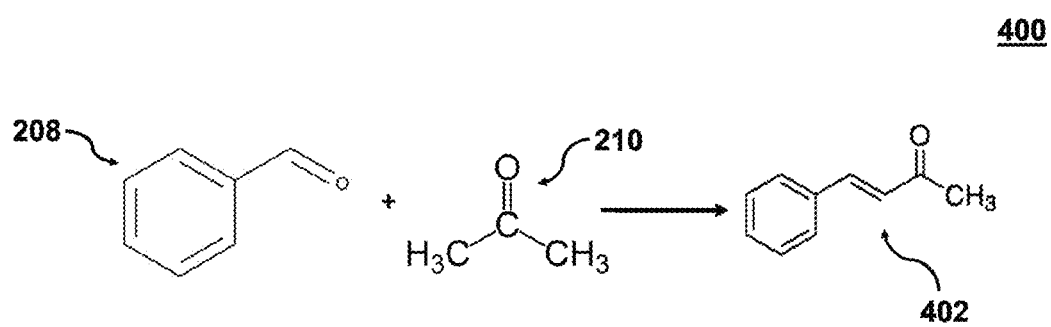
FIG. 4 illustrates an exemplary schematic representation for forming Benzalacetone through an exemplary reaction between benzaldehyde and acetone, consistent with one or more exemplary embodiments of the present disclosure.

(w/w). In an exemplary embodiment, an exemplary liquid mixture may comprise acetone with an exemplary concentration of about 7.1% (w/w). In one or more exemplary embodiment, acetone may be substituted with acetophenone, 4-acetophenone, 4-methoxyacetophenone, 4-methylacetophenone. In an exemplary embodiment, an exemplary reaction may be occurred, in an exemplary laboratory container, between benzaldehyde and acetone resulting in the formation of Benzalacetone. FIG. 4 illustrates exemplary schematic representation 400 for forming Benzalacetone 402 through an exemplary reaction between benzaldehyde 208 and acetone 210, consistent with one or more exemplary embodiments of the present disclosure.

Referring back to step 102, in one or more exemplary embodiments, an exemplary liquid mixture may comprise trihexyltetradecylphosphonium bromide with a concentration between about 50.5% (w/w) and 53% (w/w). In an exemplary embodiment, an exemplary liquid mixture may comprise trihexyltetradecylphosphonium bromide with an exemplary concentration of about 51.9% (w/w). In one or more exemplary embodiments, trihexyltetradecylphosphonium bromide may be configured to catalyze an exemplary reaction between 4-Hydroxycoumarin 302 and Benzalacetone 402 (see FIGS. 3 and 4, respectively) by ionizing an exemplary carbonyl group in 4-Hydroxycoumarin 302.

In an exemplary implementation, an exemplary liquid mixture of step 102 may be prepared by adding a powder and/or a liquid of methyl salicylate, acetyl chloride, benzaldehyde, and acetone (e.g., using a spatula, a graduated cylinder, a pipet, etc.) to an exemplary ionic liquid of trihexyltetradecylphosphonium bromide, while stirring at about 20-25° C. using a magnetic stirrer, so that the final concentration of methyl salicylate, acetyl chloride, benzaldehyde, and acetone in an exemplary mixture of step 102 may become about 17.5-19.5% (w/w), about 8.5-10.5% (w/w), about 11.5-14% (w/w), and about 6.5-7.5% (w/w), respectively. In an exemplary embodiment, an exemplary liquid mixture may comprise trihexyltetradecylphosphonium bromide with an exemplary final concentration of about 50.5% (w/w) to 53% (w/w). For example, in an exemplary embodiment, methyl salicylate, acetyl chloride, benzaldehyde, acetone, and trihexyltetradecylphosphonium may have an exemplary molar ratio of about 1:1:1:1:1 in an exemplary liquid mixture of step 102.

Figure 5:
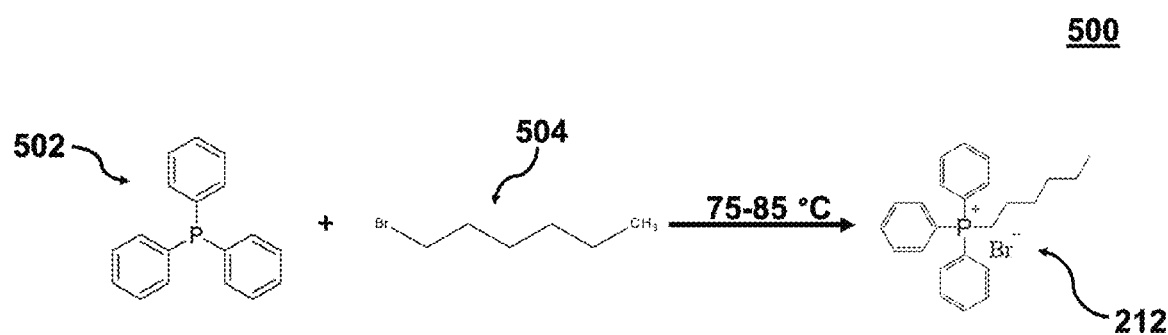
FIG. 5 illustrates an exemplary schematic representation for forming an exemplary ionic liquid of trihexyltetradecylphosphonium bromide, consistent with one or more exemplary embodiments of the present disclosure.

In an exemplary embodiment, an exemplary ionic liquid of trihexyltetradecylphosphonium may be produced by reacting Triphenylphosphine with Bromohexane. FIG. 5 illustrates exemplary schematic representation 500 for forming an exemplary ionic liquid of trihexyltetradecylphosphonium bromide 212, consistent with one or more exemplary embodiments of the present disclosure. In an exemplary embodiment, as shown in FIG. 5, exemplary ionic liquid of trihexyltetradecylphosphonium bromide 212 may be prepared by reacting Triphenylphosphine 502 with Bromohexane 504 at an exemplary temperature ranging between about 75° C. and 85° C. In an exemplary embodiment, Triphenylphosphine 502 may be reacted with Bromohexane 504 in ethanol as an exemplary solvent. In an exemplary embodiment, exemplary ionic liquid of trihexyltetradecylphosphonium bromide 212 may be prepared by reacting Triphenylphosphine 502 with Bromohexane 504 while being stirred (using a stirrer) at an exemplary temperature of about 80° C. for an exemplary time duration of about 3 hours. In an exemplary embodiment, Triphenylphosphine 502 and Bromohexane 504 may be added to an exemplary ethanol solvent with a weight ratio (Triphenylphosphine 502:Bromohexane 504) of about 1:1. For example, in an exemplary implementation, to prepare about 10 mL of an exemplary ionic liquid of trihexyltetradecylphosphonium, about 1 mmol of Triphenylphosphine and about 1 mmol of Bromohexane may be added to about 10 mL acetone, in an exemplary laboratory container (e.g., a beaker), and may be stirred at about 80° C. for about 3 hours.

With further reference to FIG. 1, step 104 may include incubating an exemplary liquid mixture (i.e., an exemplary liquid mixture set forth in step 102) at an exemplary predetermined temperature. In an exemplary embodiment, incubating an exemplary liquid mixture at an exemplary predetermined temperature may include incubating an exemplary liquid mixture at an exemplary temperature between about 20° C. and 30° C. for an exemplary time duration between about 26 and 34 minutes. In an exemplary embodiment, incubating an exemplary liquid mixture at an exemplary predetermined temperature may include stirring/mixing an exemplary liquid mixture for an exemplary time duration of about 30 minutes while an exemplary temperature of an exemplary liquid mixture is maintained at an exemplary temperature ranging between 20° C. and 30° C., e.g., using a stirring incubator.

Referring again to FIG. 1, step 106 may include forming an exemplary (RS)-Warfarin by adding water to an exemplary incubated liquid mixture. In an exemplary embodiment, forming an exemplary (RS)-Warfarin by adding water to an exemplary incubated liquid mixture may include forming an exemplary (RS)-Warfarin, in form of exemplary crystalline solids, by adding distilled water or double-distilled water or ultrapure water to an exemplary incubated liquid mixture. In an exemplary implementation, adding water to an exemplary incubated liquid mixture may include adding distilled water or double-distilled water or ultrapure water to an exemplary incubated liquid mixture with a volume ratio (water:incubated liquid mixture) between 1:1 and 1.5:1. In an exemplary implementation, adding water to an exemplary incubated liquid mixture may include adding distilled water or double-distilled water or ultrapure water to an exemplary incubated liquid mixture with a volume ratio (water:incubated liquid mixture) of about 1:1 (e.g., adding about 10 mL water to about 10 mL of an exemplary incubated liquid mixture). "Ultrapure water" may refer to a water that has been purified using a combination of ultrafiltration technologies and ultraviolet photo-oxidation system. An ultrapure water may be RNase-free and/or pyrogen-free, and may be ultra-low in organics.

In one or more exemplary embodiments, exemplary crystalline solids of (RS)-Warfarin may be isolated by filtering the resulting mixture of water with an exemplary incubated liquid mixture through a filter paper. In one or more exemplary embodiments, one or more exemplary chromatographic techniques may be used to yield an exemplary highly purified (RS)-Warfarin. Exemplary chromatographic techniques may include, but are not limited to, thin layer chromatography (TLC) and/or column chromatography. In an exemplary embodiment, an exemplary (RS)-Warfarin may be isolated through an exemplary silica gel TLC, followed by recrystallization. For example, in an exemplary implementation, the formed exemplary (RS)-Warfarin in step 106 of exemplary method 100 may be dissolved in ethyl acetate and dropped onto an exemplary Silica TLC Plate (e.g., a glass-backed TLC plate with 250-μm thickness and 20×20 cm dimensions). In an exemplary implementation, an exemplary solvent mix of hexane:ethyl acetate with a molar ratio of about 4:1 may be used as an exemplary mobile phase in TLC of an exemplary (RS)-Warfarin. In an exemplary embodiment, an exemplary silica gel TLC may result in the appearance of a plurality of bands on an exemplary TLC plate including, but not limited to, a trihexyltetradecylphosphonium bromide band, a methyl salicylate band, an acetyl chloride band, a benzaldehyde band, an acetone band, a Benzalacetone band, a 4-Hydroxycoumarin band, and a (RS)-Warfarin band. An exemplary (RS)-Warfarin band may be scraped from an exemplary TLC plate, and ethyl acetate may be added to the scraped band, while stirring using a stirrer, e.g., a magnetic stirrer. An exemplary mixture of the scraped band and ethyl acetate may, subsequently, be filtered and ethyl acetate may be removed by rotary evaporation, resulting in precipitation of a white solid that may comprise (RS)-Warfarin crystals. In an exemplary embodiment, an exemplary TLC may result in the formation of an exemplary (RS)-Warfarin with at least 90%, at least 93%, at least 95%, at least 98%, and/or at least 99% purity.

Figure 6:
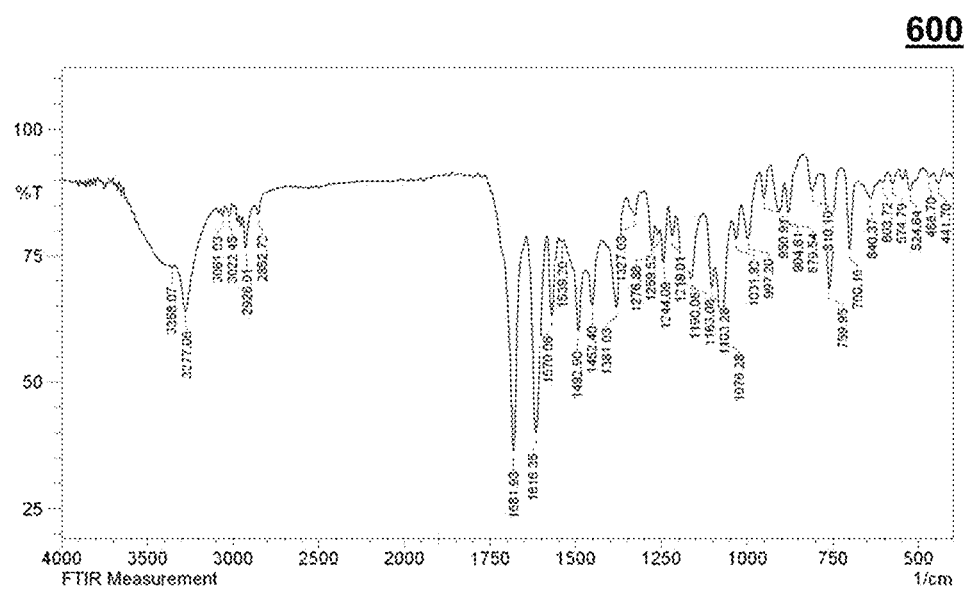
FIG. 6 illustrates an exemplary Fourier-Transform Infrared (FTIR) spectrum of an exemplary (RS)-Warfarin, consistent with one or more exemplary embodiments of the present disclosure.

In one or more exemplary embodiments, an exemplary (RS)-Warfarin may be prepared as an exemplary pharmaceutically acceptable Warfarin derivative, including but not limited to, exemplary Warfarin salts (e.g., Warfarin potassium, Warfarin sodium, etc.) and Warfarin clathrates. In one or more exemplary embodiments, an exemplary (RS)-Warfarin may be produced in different exemplary dosage forms, including but not limited to, tablets, capsules, geltabs, powder, granules, solution, and/or suspension. FIG. 6 illustrates exemplary Fourier-Transform Infrared (FTIR) spectrum 600 of an exemplary (RS)-Warfarin, consistent with one or more exemplary embodiments of the present disclosure. FTIR analysis may be used to characterize and confirm the formation of exemplary (RS)-Warfarin. Referring to FIG. 6, exemplary FTIR spectrum 600 of exemplary (RS)-Warfarin may exhibit a peak at 3277.06 cm$^{-1}$ which may indicate the presence of an exemplary hydroxyl group in an exemplary structure of (RS)-Warfarin. Meanwhile, exemplary peaks at wavelengths of about 1616.35 cm$^{1}$ and 1681.93 cm$^{-1}$ may indicate the presence of an exemplary carbonyl group in an exemplary structure of (RS)-Warfarin.

Figure 7:
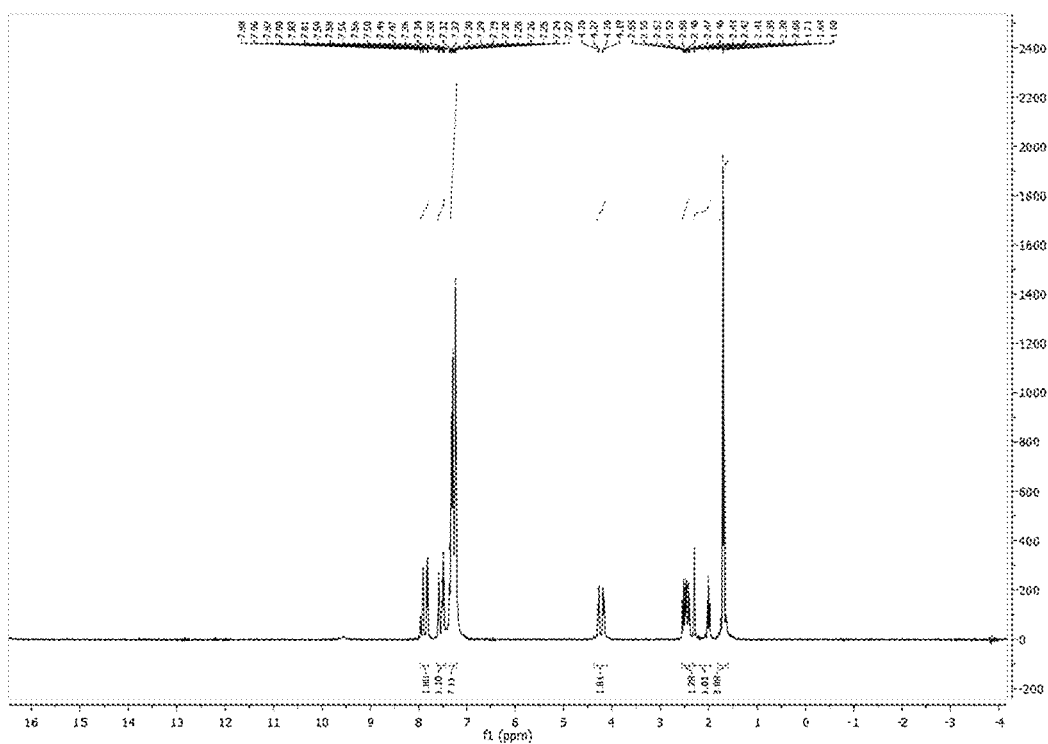
FIG. 7 illustrates an exemplary proton nuclear magnetic resonance ($^1$H NMR) spectrum of an exemplary (RS)-Warfarin, consistent with one or more exemplary embodiments of the present disclosure.

FIG. 7 illustrates exemplary proton nuclear magnetic resonance ($^1$H NMR) spectrum 700 of an exemplary (RS)-Warfarin, consistent with one or more exemplary embodiments of the present disclosure. $^1$H NMR technique may employ nuclear magnetic resonance to identify or confirm an exemplary structure of an organic compound or exemplary compounds that may have protons. Referring to FIG. 7, exemplary $^1$H NMR spectrum 700 may be consistent with an exemplary structure of (RS)-Warfarin. Referring to exemplary $^1$H NMR spectrum 700, an exemplary singlet may be observed at 1.69 ppm that may correspond to exemplary methyl protons of exemplary (RS)-Warfarin; two exemplary doublets may be observed at 2.15 ppm (J=5.0, 5.0 Hz) and 3.47 ppm (J=5.0, 5.0 Hz) that may correspond to exemplary methylene protons (H2 and H'2, respectively) of exemplary (RS)-Warfarin; an exemplary doublet may be observed at 4.18 ppm (J=5.0, 5.0 Hz) that may correspond to an exemplary methine proton (H1) of exemplary (RS)-Warfarin; and exemplary multiplets may be observed at 7.22-7.36 ppm, 7.47-7.59 ppm, and 7.81-7.98 ppm that may correspond to exemplary aromatic protons of exemplary (RS)-Warfarin.

EXAMPLES

Hereinafter, one or more exemplary embodiments will be described in further detail with reference to examples. It will be obvious to a person having ordinary skill in the art that these examples may be for illustrative purposes only and are not to be interpreted to limit the scope of the present disclosure.

Example 1: Monitoring Anticoagulation Effect of an Exemplary (RS)-Warfarin

In this example, the anticoagulation effect of an exemplary (RS)-Warfarin was evaluated by an exemplary prothrombin time (PT) test. PT test may refer to an exemplary method carried out for monitoring oral anticoagulant therapy. PT test may measure the period of time it takes for a clot to form in a blood sample. In particular, PT test may measure the activity of exemplary coagulation factors involved in one or more exemplary extrinsic and common coagulation pathways. In one or more exemplary embodiments, prothrombin time may increase in response to inhibition of vitamin K-dependent procoagulant clotting factors (i.e., exemplary factors VII and X and prothrombin).

In an exemplary implementation, PT test may be accomplished in an animal model and may be compared to an exemplary commercial sample of Warfarin. In an exemplary implementation, 24 male rats were randomly separated into four groups, six rats in each group. Group I received distilled water (Control Group), Group II received an exemplary commercial Warfarin with an exemplary dose of 5 mg commercial Warfarin per weight of each rat (5 mg/kg), Group III received an exemplary synthesized (RS)-Warfarin with an exemplary dose of 5 mg (RS)-Warfarin per weight of each rat (5 mg/kg (Dose 1)), and Group IV received synthesized (RS)-Warfarin with an exemplary dose of 10 mg (RS)-Warfarin per weight of each rat (10 mg/kg (Dose 2)).

In an exemplary implementation, PT test was performed by feeding exemplary commercial Warfarin and Dose 1 of exemplary synthesized (RS)-Warfarin to Group II and Group III of rats, respectively. After 24 hours, exemplary blood samples were collected from two rats that were randomly selected from each of Group II and Group III. About 1.8 ml of each blood sample was added to exemplary tubes containing an exemplary anticoagulant, sodium citrate dihydrate. After centrifugation of each citrated blood sample at 2000 gr for 15 minutes, plasma was separated to be used for PT analysis. In an exemplary implementation, PT test may be performed by adding a mixture of thromboplastin and calcium to citrated plasma. Thromboplastin is a protein-phospholipid extract of tissue that may contain necessary phospholipids and tissue factors for promoting activation of factor X by factor VII. At the beginning of an exemplary anticoagulant therapy (e.g., Warfarin therapy), prothrombin time may reflect an exemplary depression of factor VII, because factor VII may have the shortest half-life among exemplary vitamin K-dependent factors. During an exemplary maintenance therapy, PT test may be sensitive to the decrease in prothrombin and factor X levels. PTs and international normalized ratios (INRs) were measured for Group II and Group III of rats. Table 1 shows exemplary PTs (prothrombin times) and international normalized ratios (INRs) measured for Groups II and Group III rats' blood samples, consistent with one or more exemplary embodiments. Comparing exemplary PTs and INRs measured for Group II and Group III blood samples may show that exemplary synthesized (RS)-Warfarin may have a significantly increased anticoagulant effect in comparison to exemplary commercial Warfarin.

TABLE 1

Exemplary PTs (prothrombin times) and INRs measured for Groups II and Group III rats' blood samples, consistent with one or more exemplary embodiments of the present disclosure.

| Exemplary Blood Samples | Prothrombin Time (seconds) | International Normalized Ratio |
|---|---|---|
| Exemplary Synthesized (RS)-Warfarin | 24.4 | 3.4 |
| Exemplary Commercial Warfarin | 18.6 | 2.19 |

Example 2: Assessing Toxicity of Exemplary (RS)-Warfarin by Clinical Chemistry Tests In this example, toxicity of exemplary (RS)-Warfarin was assessed using one or more exemplary clinical chemistry tests, such as urea test, creatinine test, SGOT (glutamic oxaloacetic transaminase) test, SGPT (glutamate-pyruvate transaminase) test, and LDH (lactate dehydrogenase) test. In an exemplary implementation, Group II, Group III, and Group IV of rats were fed with exemplary commercial Warfarin, Dose 1 of exemplary synthesized (RS)-Warfarin, and Dose 2 of exemplary synthesized (RS)-Warfarin, respectively. After 24 hours, exemplary blood samples were collected from three rats that were randomly selected from each of the Groups I-IV (i.e., 12 rates were selected in total).

Figure 8:
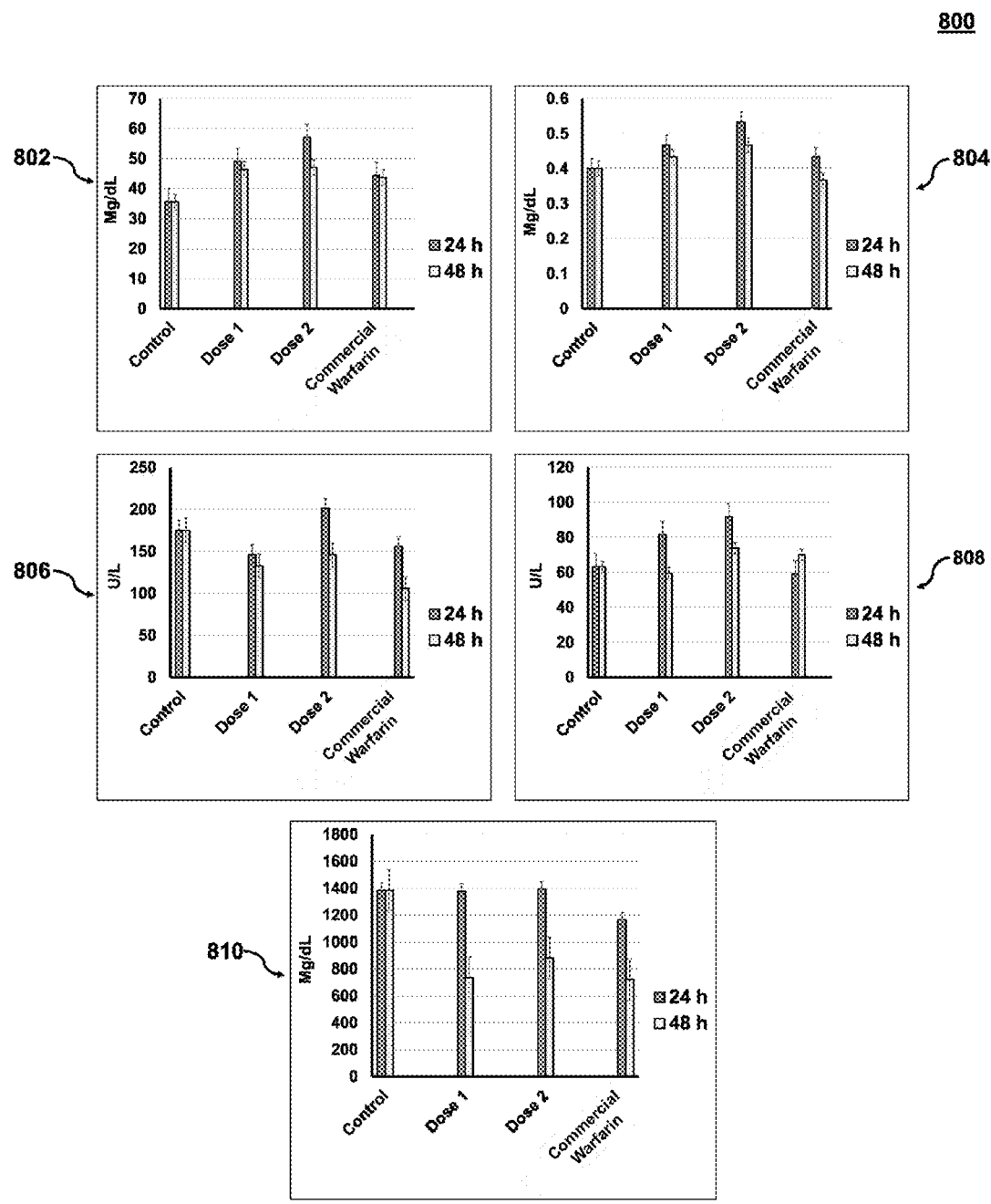
FIG. 8 illustrates exemplary biochemical test results for urea test, creatinine test, SGOT test, SGPT test, and LDH test performed to monitor exemplary toxic effects of an exemplary synthesized (RS)-Warfarin compared to an exemplary commercial Warfarin, consistent with one or more exemplary embodiments of the present disclosure.

After euthanization of the selected rats, about 4 ml blood was collected from each rat to be tested for urea, creatinine, SGOT, SGPT, and LDH. FIG. 8 illustrates exemplary biochemical test results 800 for urea test 802, creatinine test 804, SGOT test 806, SGPT test 808, and LDH test 810 performed to monitor exemplary toxic effects of exemplary synthesized (RS)-Warfarin compared to an exemplary commercial Warfarin, consistent with one or more exemplary embodiments of the present disclosure. With reference to FIG. 8, exemplary test results obtained from exemplary rats fed with exemplary synthesized (RS)-Warfarin may not significantly differ from exemplary test results obtained from exemplary rats fed with exemplary commercial Warfarin.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. An element proceeded by "a" or "an" does not, without further constraints, preclude the existence of additional identical elements in the process, method, article, or apparatus that comprises the element.

Unless otherwise stated, all measurements, values, ratings, positions, magnitudes, sizes, and other specifications that are set forth in this specification, are approximate, not exact. They are intended to have a reasonable range that is consistent with the functions to which they relate and with what is customary in the art to which they pertain.

It will be understood that the terms and expressions used herein have the ordinary meaning as is accorded to such terms and expressions with respect to their corresponding respective areas of inquiry and study, except where specific meanings have otherwise been set forth herein. Relational terms such as "first" and "second" and the like may be used solely to distinguish one entity or action from another without necessarily requiring or implying any actual such relationship or order between such entities or actions.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it may be seen that various features are grouped together in various implementations. This is for purposes of streamlining the disclosure, and is not to be interpreted as reflecting an intention that the claimed implementations require more features than are expressly recited in each claim. Rather, as the following claims reflect, inventive subject matter lies in less than all features of a single disclosed implementation. Thus, the following claims are hereby incorporated into the Detailed Description, with each claim standing on its own as a separately claimed subject matter.

While various implementations have been described, the description is intended to be exemplary, rather than limiting and it will be apparent to those of ordinary skill in the art that many more implementations and implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown and/or discussed in the present disclosure may be implemented together in any suitable combination. Accordingly, the implementations are not to be restricted except in light of the attached claims and their equivalents. Also, various modifications and changes may be made within the scope of the attached claims.

What is claimed is:

1. A method for synthesizing (RS)-Warfarin, comprising:
preparing a liquid mixture comprising:
trihexyltetradecylphosphonium bromide with a concentration between 50.5% (w/w) and 53% (w/w);
methyl salicylate with a concentration between 17.5% (w/w) and 19.5% (w/w);
acetyl chloride with a concentration between 8.5% (w/w) and 10.5% (w/w);
benzaldehyde with a concentration between 11.5% (w/w) and 14% (w/w); and
acetone with a concentration between 6.5% (w/w) and 7.5% (w/w);
incubating the liquid mixture at a temperature between 20° C. and 30° C. for a time duration between 26 and 34 minutes; and
forming the (RS)-Warfarin by adding water to the incubated liquid mixture with a volume ratio (water:incubated liquid mixture) between 1:1 and 1.5:1.

2. A method for synthesizing (RS)-Warfarin, comprising:
preparing a liquid mixture consisting of:
trihexyltetradecylphosphonium bromide;
methyl salicylate;
acetyl chloride;
benzaldehyde; and
acetone;
incubating the liquid mixture at a temperature between 20° C. and 30° C. for a time duration between 26 and 34 minutes; and
forming the (RS)-Warfarin by adding water to the incubated liquid mixture with a volume ratio (water:incubated liquid mixture) between 1:1 and 1.5:1.

3. The method of claim 2, wherein the trihexyltetradecylphosphonium bromide has a concentration between 50.5% (w/w) and 53% (w/w).

4. The method of claim 3, wherein the trihexyltetradecylphosphonium bromide has a concentration of 51.9% (w/w).

5. The method of claim 2, wherein the methyl salicylate has a concentration between 17.5% (w/w) and 19.5% (w/w).

6. The method of claim 5, wherein the methyl salicylate has a concentration of 18.5% (w/w).

7. The method of claim 2, wherein the acetyl chloride has a concentration between 8.5% (w/w) and 10.5% (w/w).

8. The method of claim 7, wherein the acetyl chloride has a concentration of 9.6% (w/w).

9. The method of claim 2, wherein the benzaldehyde has a concentration between 11.5% (w/w) and 14% (w/w).

10. The method of claim 9, wherein the benzaldehyde has a concentration of 12.9% (w/w).

11. The method of claim 2, wherein the acetone has a concentration between 6.5% (w/w) and 7.5% (w/w).

12. The method of claim 11, wherein the acetone has a concentration of 7.1% (w/w).

13. The method of claim 2, wherein preparing the liquid mixture comprises preparing the liquid mixture comprising:
the trihexyltetradecylphosphonium bromide with a concentration between 50.5% (w/w) and 53% (w/w);
the methyl salicylate with a concentration between 17.5% (w/w) and 19.5% (w/w);
the acetyl chloride with a concentration between 8.5% (w/w) and 10.5% (w/w);
the benzaldehyde with a concentration between 11.5% (w/w) and 14% (w/w); and
the acetone with a concentration between 6.5% (w/w) and 7.5% (w/w).

* * * * *